United States Patent
Grass et al.

(10) Patent No.: US 12,053,334 B2
(45) Date of Patent: Aug. 6, 2024

(54) IMAGE GUIDANCE FOR IMPLANTED LEAD EXTRACTION

(71) Applicant: KONINKLIJKE PHILIPS N.V., Eindhoven (NL)

(72) Inventors: Michael Grass, Buchholz In der Nordheide (DE); Dirk Schaefer, Hamburg (DE); Christian Haase, Hamburg (DE); Wade Allen Bowe, Colorado Springs, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 715 days.

(21) Appl. No.: 17/279,269

(22) PCT Filed: Sep. 20, 2019

(86) PCT No.: PCT/EP2019/075268
§ 371 (c)(1),
(2) Date: Mar. 24, 2021

(87) PCT Pub. No.: WO2020/064518
PCT Pub. Date: Apr. 2, 2020

(65) Prior Publication Data
US 2021/0401534 A1 Dec. 30, 2021

Related U.S. Application Data

(60) Provisional application No. 62/736,247, filed on Sep. 25, 2018.

(30) Foreign Application Priority Data

Oct. 10, 2018 (EP) .................................... 18199512

(51) Int. Cl.
*A61B 90/00* (2016.01)
*A61B 6/00* (2006.01)

(52) U.S. Cl.
CPC ................. *A61B 90/37* (2016.02); *A61B 6/00* (2013.01); *A61B 2090/365* (2016.02); *A61B 2090/3762* (2016.02)

(58) Field of Classification Search
CPC ......... A61B 6/486; A61B 6/5217; A61B 1/00; A61B 1/0002; A61B 1/005; A61B 1/313;
(Continued)

(56) References Cited

U.S. PATENT DOCUMENTS

| 2003/0092995 A1 | 5/2003 | Thompson |
| 2009/0105779 A1 | 4/2009 | Moore |

(Continued)

FOREIGN PATENT DOCUMENTS

| EP | 3284420 A1 | 2/2018 |
| JP | 2017217474 A | 12/2017 |

(Continued)

OTHER PUBLICATIONS

International Search Report and Written Opinion of PCT/EP2019/075268, dated Nov. 28, 2019.

*Primary Examiner* — Don K Wong

(57) ABSTRACT

The present invention relates to a device (1) for providing image data during an extraction procedure for extracting a lead from the body of a subject using an extraction device (7). The device comprises an input (2) for receiving live x-ray projection image data of the lead during the extraction procedure and for receiving three-dimensional image data as acquired before the extraction procedure. A processing unit (3) determines a position of the extraction device (7) in the three-dimensional image data by detecting the position in the live projection image data during the procedure and correlates this position in the live projection image data with the position in the three-dimensional image data. An output (4) generates an image of a cross-sectional view of the lead (Continued)

and/or its surrounding body structure at the determined position based on the three-dimensional image data.

20 Claims, 5 Drawing Sheets

(58) Field of Classification Search
CPC .... A61B 1/32; A61B 6/12; A61B 6/42; A61B 6/48; A61B 6/547; A61B 6/5223
See application file for complete search history.

(56) References Cited

U.S. PATENT DOCUMENTS

| | | |
|---|---|---|
| 2009/0310847 A1 | 12/2009 | Matsuzaki |
| 2011/0178543 A1 | 7/2011 | Chin |
| 2013/0322724 A1 | 12/2013 | Florent |
| 2014/0081252 A1 | 3/2014 | Bowe |
| 2017/0007350 A1 | 1/2017 | Popovic |
| 2017/0347980 A1 | 12/2017 | Wakai |

FOREIGN PATENT DOCUMENTS

| | | | |
|---|---|---|---|
| JP | 7366127 B2 * | 10/2023 | ............ A61B 6/032 |
| WO | 2007113705 A1 | 10/2007 | |

\* cited by examiner

IMAGE GUIDANCE FOR IMPLANTED LEAD EXTRACTION

CROSS-REFERENCE TO PRIOR APPLICATIONS

This application is the U.S. National Phase application under 35 U.S.C. § 371 of International Application No. PCT/EP2019/075268, filed on Sep. 20, 2019, which claims the benefit of U.S. Provisional Patent Application Ser. No. 62/736,247, filed Sep. 25, 2018 and European Patent Application No. 18199512.7, filed on Oct. 10, 2018. These applications are hereby incorporated by reference herein.

FIELD OF THE INVENTION

The invention relates to the field of diagnostic imaging and image guided therapy in medicine. More specifically it relates to a device, system and method for providing image data during an extraction procedure for extracting a lead from the body of a subject using an extraction device.

BACKGROUND OF THE INVENTION

The extraction of a surgically implanted cardiac device, such as a pacemaker or a defibrillator, may be required under certain conditions, such as in cases of malfunction or infection. The removal of such devices may potentially imply a high risk procedure. Particularly, a wire or wires, commonly referred to as leads, typically run from a control unit, e.g. a pulse signal generator, to the heart. In a pacemaker, these leads enable the device to influence the heart rate by delivering a train of electric pulses, while in a defibrillator, the lead may be adapted for delivering a high-energy pulse to the heart to disrupt a dangerous fibrillation condition.

The lead typically runs through a vein to the heart. The tip of the lead may typically be anchored to the heart muscle, e.g. by tines, a screw or hook and, after a few months after implantation, scar tissue.

The extraction of pacemaker or defibrillator leads can be performed by various tools including simple sheaths, a laser-based extraction device or a rotating mechanical cutting device. In order to plan and execute the lead extraction, there is a desire for information about the amount and location of calcifications and/or about the adhesion and/or compliance of the lead to the vascular bed. Therefore, high quality visualization of the anatomy close to the lead can offer valuable support to the procedure execution.

SUMMARY OF THE INVENTION

It is an advantage of embodiments of the present invention to provide good, efficient and useful image guidance during a procedure of extracting an implanted lead(s), e.g. of a pacemaker or defibrillator.

It is an advantage of embodiments of the present invention that 3D image data, such as a CT volumetric image can be visualized during an extraction intervention. For example, local diagnostic three-dimensional image information at the location of an extraction device tip can be provided during the extraction procedure.

It is an advantage of embodiments of the present invention that the safety of the extraction procedure can be increased, for example by making relevant information readily available during the procedure and/or by controlling an extraction device based on information derived from 3D image data, such as a CT volumetric image.

It is an advantage of embodiments of the present invention that during the extraction procedure (or before the extraction procedure, for reference during the procedure) it can easily be determined from the provided image or images how close to the vessel wall the lead body is at any location, such as at the location of the extraction device.

It is an advantage of embodiments of the present invention that during the extraction procedure it can easily be determined from the provided image or images how close to the vessel wall the lead body is at the location of the extraction device.

It is an advantage of embodiments of the present invention that during the extraction procedure it can easily be determined from the provided image or images if the extraction device is near the lead tip, e.g. near an embedded tip of the lead.

It is an advantage of embodiments of the present invention that during the extraction procedure (or before the extraction procedure, for reference during the procedure) it can easily be determined from the provided image or images if lead-to-lead binding could be present, e.g. based on how a contrast agent flows between leads and the location of the leads relative to each other.

In a first aspect, the present invention relates to a device for providing image data during an extraction procedure for extracting a lead from the body of a subject using an extraction device, e.g. a lead in a blood vessel of the body. The device comprises an input for receiving a live stream of x-ray projection image data of the lead in the body of the subject during the extraction procedure and for receiving three-dimensional image data representative of the lead in the body of the subject as acquired before performing the extraction procedure. The device comprises a processing unit for determining a position of the extraction device in (the coordinate system of) the three-dimensional image data by detecting a position of the extraction device in the live stream of x-ray projection image data during the extraction procedure and correlating the position in the live stream with the position in the three-dimensional image data.

The device comprises an output comprising an interface configured to control at least one parameter of said extraction device. The processing unit is further adapted i) to determine a vessel and/or plaque characteristic at or near said determined position of said extraction device and ii) to control said at least one parameter of said extraction device by taking said characteristic into account.

In a device in accordance with embodiments of the present invention, the output is further adapted to generate and output an image of a cross-sectional view of the lead and/or its surrounding body structure, such as e.g. a blood vessel or heart chamber, at the determined position based on the three-dimensional image data. For example, the three-dimensional image data may be pre-interventional image data. For example, the three-dimensional image data may be computed tomography (CT) data, C-arm CT data and/or cone beam CT data.

In a device in accordance with embodiments of the present invention, the output may be adapted for generating and outputting a plurality of images of cross-sectional views of the lead and/or its surrounding body structure at a plurality of locations spaced forward from or spaced around the determined position of the extraction device in the three-dimensional image data in the longitudinal direction of the blood vessel, e.g. locations along a central axis of the blood vessel, and/or of the longitudinal direction of the lead.

In a device in accordance with embodiments of the present invention, the output may be adapted for generating and outputting a further image of a longitudinal view of the lead and/or its surrounding body structure at the determined position of the extraction device based on the three-dimensional image data.

In a device in accordance with embodiments of the present invention, the output may comprise an interface for controlling at least one parameter of the extraction device. The processing unit may be adapted for determining a vessel and/or plaque characteristic at or near the determined position of the extraction device and for controlling the at least one parameter by taking the characteristic into account. The at least one parameter of the extraction device may comprise a power setting and/or an on/off setting of said extraction device.

In a device in accordance with embodiments of the present invention, the processing unit may be adapted for deactivating the extraction device when the detected position corresponds to a region with low adhesion and/or a softer region after a hard plaque.

A device in accordance with embodiments of the present invention may comprise a pre-processor for processing the three-dimensional image data. This processing may comprise segmenting the lead from the three-dimensional image data to provide a segmented three-dimensional image.

In a device in accordance with embodiments of the present invention, the processing unit may be adapted for registering the segmented three-dimensional image to the live stream of x-ray projection image data to correlate the detected position of the extraction device in the live stream of x-ray projection image data with the position in the three-dimensional image data.

In a device in accordance with embodiments of the present invention, the pre-processor may be adapted for fitting a three-dimensional parametric model of the lead to the segmented three-dimensional image such that the fitted three-dimensional parametric model is representative of the spatial configuration of the lead as present in the body of the subject before performing the extraction procedure. The processing unit may be adapted for registering the fitted three-dimensional parametric model to the live stream of x-ray projection image data to correlate the detected position of the extraction device in the live stream of x-ray projection image data with the position in the three-dimensional image data.

In a device in accordance with embodiments of the present invention, the pre-processor may be adapted for determining a parameter as function of a longitudinal position along the lead based on the three-dimensional image data and/or the fitted three-dimensional parametric model. The output may be adapted for outputting the parameter corresponding to a longitudinal position at or ahead of the determined position of the extraction device. This parameter may comprise a local curvature and/or a degree of local adhesion of the lead and/or a proximity of the lead to the vessel wall.

In a device in accordance with embodiments of the present invention, the pre-processor may be adapted for determining the degree of local adhesion to the vessel wall by quantifying a local motion of the lead relative to the vessel wall from a temporal sequence of three-dimensional image data received via the input and determining a degree of local adhesion based on the local motion.

In a device in accordance with embodiments of the present invention, the three-dimensional image data may comprise a contrast-enhanced cardiac computed tomography dataset of the thorax and the heart of the subject.

In a second aspect, the present invention relates to an integrated system for providing information and/or for controlling equipment in an operating room, interventional radiology room or heart catherization laboratory, the system comprising a device in accordance with embodiments of the first aspect of the present invention.

A system in accordance with embodiments of the present invention may comprise the extraction device.

In a third aspect, the present invention relates to a method, e.g. a computer-implemented method, for providing image data during an extraction procedure for extracting a lead, e.g. in a blood vessel or heart chamber, from the body of a subject using an extraction device. The method comprises receiving three-dimensional image data representative of the lead in the body of the subject as acquired before performing the extraction procedure. The method comprises receiving a live stream of x-ray projection image data of the lead in the body of the subject during the extraction procedure. The method comprises determining a position of the extraction device in the three-dimensional image data by detecting a position of the extraction device in the live stream of x-ray projection image data during the extraction procedure and correlating said position in the live stream with said position in the three-dimensional image data. The method comprises generating and outputting an image of a cross-sectional view of the lead and/or its surrounding body structure at the determined position based on the three-dimensional image data.

In a further aspect, the present invention also relates to a computer program product for performing a method in accordance with embodiments of the third aspect of the present invention when executed on a computing device.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
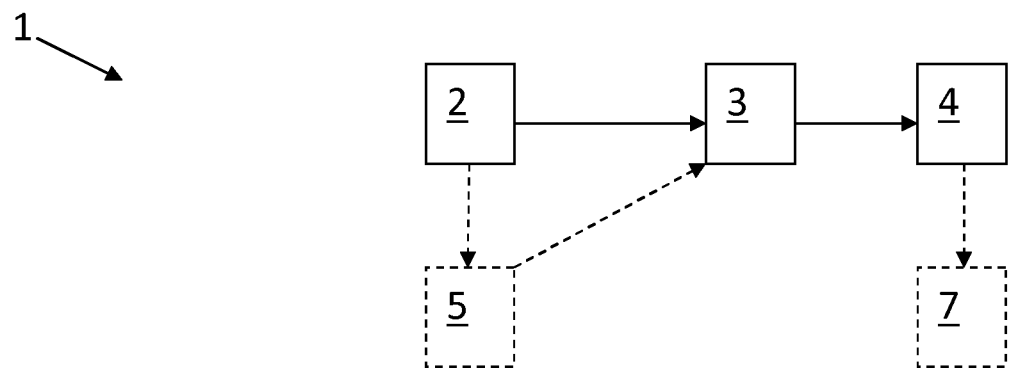
FIG. 1 schematically illustrates a device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a device for providing image data for use during an extraction procedure for extracting a lead, e.g. in a blood vessel or heart chamber, from the body of a subject using an extraction device. The device comprises a processing unit, an input and an output. The input is adapted for receiving a live stream of x-ray projection image data of the lead in the body of the subject during the extraction procedure. The input is also adapted for receiving three-dimensional image data representative of the lead in the body of the subject as acquired before performing the extraction procedure. The processing unit is adapted, e.g. programmed, for determining, e.g. continuously or frequently updating, a position of the extraction device in the live stream of x-ray projection image data during the extraction procedure. The processing unit is also adapted for correlating the position in the live stream with a position in the three-dimensional image data, i.e. such that the position of the extraction device is determined in (i.e. in the coordinate system of) the three-dimensional image data. The output is adapted for generating and outputting an image of a cross-sectional view of the lead and/or its surrounding body structure, e.g. a blood vessel or heart chamber, at the determined position based on the three-dimensional image data.

Referring to FIG. 1, a device 1 in accordance with embodiments of the first aspect of the present invention is shown. The device 1 is adapted for providing image data, e.g. augmented image information, during an extraction procedure for extracting at least one lead from the body of a subject, e.g. an implanted lead, e.g. a lead wire such as a conductive wire of a pacemaker, a defibrillator, neurostimulator and/or an electric potential sensor. Thus, the device may be adapted for providing image guidance during the extraction procedure, e.g. during a procedure for extracting at least one lead that connects a defibrillator or pacemaker to the heart muscle to deliver a signal to the heart muscle. The device may be adapted for making image information available in an interventional radiology (IR), heart catherization laboratory (CathLab), or operating room (OR). For example, the device 1 may comprise an IR or CathLab system (e.g. the involved imaging system may be a ceiling mounted C-arm system, a floor mounted C-arm system, a bi-plane C-arm system, a mobile C-arm system or a robotic X-ray system comprising an X-ray source and detector), e.g. an integrated system for providing information and controlling equipment in such OR, IR or CathLab room. The device 1 may also comprise the extraction device 7. The extraction device 7 may comprise a tissue dissecting, slitting or cutting device for removing the implanted lead from within the vascular system of the body, as known in the art. The extraction device 7 may comprise a cutting device for cutting the lead from embedding tissue by mechanical force and/or by delivering energy by means of a laser device and/or by means of a radiofrequency source.

The device 1 comprises an input 2. The input 2 is adapted for receiving a live stream of x-ray projection image data of at least part of the body of the subject during the extraction procedure, in which this part contains the lead to be extracted. For example, the live stream of x-ray projection image data may be a continuously or frequently updated two-dimensional x-ray projection image. For example, the live stream of x-ray projection image data may comprise x-ray fluoroscopy image data. The live stream of x-ray projection image data may comprise a live stream of images of the heart (or part thereof) of the subject, e.g. particularly when used in a procedure of extracting a lead in or near the heart.

The input 2 is furthermore adapted for receiving three-dimensional (3D) data representative of the lead in the body of the subject. Particularly, the 3D data may be obtained before the executing the extraction procedure. For example, the 3D data may be, or may be based on, image data acquired before performing the extraction procedure.

The 3D data comprises 3D image data, such as a computed tomography (CT) reconstruction image volume, of at least a part of the body of the subject that contains the lead, or that contains at least a tip of the lead, e.g. a tip that needs to be detached from a structure of the body, such as the wall of a blood vessel, in the procedure of extracting the lead. However, embodiments of the present invention are not limited thereto, e.g. the 3D image data may comprise a 3D image volume of a different modality, e.g. nuclear medicine image data, 3D echography image data, magnetic resonance imaging (MRI) data or other known medical 3D imaging modalities. Furthermore, the 3D data received by the input may also comprise a 3D model of the lead, e.g. in a parametric representation, e.g. a 3D model representative of the spatial configuration of the lead as present in the body of the subject.

The 3D image data may comprise multiple coregistered image volumes, e.g. one or more coregistered 3D reconstructions, such as a non-contrast enhanced CT image volume and a contrast-enhanced CT image volume, or multiple spectral CT image volumes, e.g. multiple spectral components or material-specific images derived therefrom. The multiple coregistered images may also comprise images of multiple imaging modalities, e.g. coregistered CT and MRI data.

The 3D image data may comprise a 3D image volume in which the lead is segmented from 3D image data. For example, the 3D image volume may comprise an image volume representative of a segmentation of the lead, e.g. in which the presence or absence of the lead at each voxel location is encoded in the voxel values. However, the voxel values may also indicate the presence or absence of, additional, other features, such as a blood vessel, a blood vessel wall, a heart muscle and/or other anatomical structures. The multiple coregistered images may comprise, e.g. in addition to at least one CT or MRI reconstructed image volume, the image volume representative of the segmentation of at least the lead. However, the 3D data may also comprise a parametric model of the lead as segmented from 3D image data.

The input 2 may be adapted for receiving an image volume(s), such as a CT reconstruction image volume or an MRI reconstruction image volume, of at least a part of the body of the subject that contains (e.g. at least the tip of) the lead.

The device may comprise a pre-processor 5 for processing the image volume(s), e.g. before executing the extraction procedure. The pre-processor 5, further discussed hereinbelow, may be adapted for segmenting the lead from the image volume or image volumes to provide the 3D image volume in which the lead is segmented from 3D image data. The pre-processor 5 may be adapted for fitting a 3D model, e.g. a parametric 3D model, to the segmented 3D image of the lead.

For example, the input 2 may be adapted for receiving a cardiac CT dataset of the thorax and the heart of the subject, e.g. including the entire lead, e.g. including a volume from a pacemaker pocket to the electrode ends. For example, the cardiac CT dataset may comprise a contrast-enhanced cardiac CT data set of the thorax and the heart. The received 3D data may be corrected for metal artefacts and/or for motion artefacts.

The pre-processor 5 may be adapted for correcting the received 3D image data for metal artefacts (e.g. due to the lead) and/or motion artefacts. It is an advantage that a good quality visualization of tissue and calcifications close to the lead without metal artefacts can thus be obtained. For example, the input may receive the 3D image data in the form of raw projection data, and the pre-processor may perform a tomographic reconstruction using an algorithm as known in the art for compensating (e.g. at least reducing) for metal artefacts and/or motion artefacts.

The pre-processor 5 may be adapted for correcting the received 3D image data for metal artefacts (e.g. due to the lead) and/or motion artefacts. It is an advantage that a good quality visualization of tissue and calcifications close to the lead without metal artefacts can thus be obtained. For example, the input may receive the 3D image data and the pre-processor may perform a machine learning based artefact removal using e.g. a trained convolutional neural network for metal artefacts and/or motion artefacts.

The pre-processor 5 may be adapted for determining parameters of interest from the segmented lead, e.g. from the 3D image volume in which the lead is segmented and/or based on the parametric 3D model. For example, a local curvature of the lead as function of a longitudinal position along the lead may be determined.

For example, a degree of local adhesion of the lead tip, and/or of the lead as function of the longitudinal position along the lead, may be determined. The input 2 may be adapted for receiving a plurality of image volumes, representative of different acquisition times in a temporal sequence, e.g. the input may be adapted for receiving a four-dimensional (4D, i.e. three spatial dimensions and a temporal dimension) CT (or MRI) dataset. The pre-processor 5 may be adapted for determining the local adhesion of the lead to the wall of the body structure that contains the lead. For example, the 4D dataset may comprise a plurality of 3D images corresponding to a plurality of points in time extending over at least one cardiac cycle and/or at least one breathing cycle, such that the local motion of the lead relative to the vessel wall, induced by the natural motion of the body, can be quantified, in which regions of the lead which shows a large motion relative to the wall, e.g. a large variability of its position relative to the wall, are indicative of a low or no adhesion, and in which regions of the lead which show a small motion relative to the wall are indicative of a high adhesion. Thus, the adhesion can be quantified or determined in a straight-forward manner.

The device 1 also comprises a processing unit 3. The processing unit 3 is adapted for determining the position of the extraction device 7 in the live stream of x-ray projection image data of the lead in the body of the subject during the extraction procedure, for example by updating the position of the extraction device for each frame of the live stream. For example, the tip of an extraction device may be tracked on the X-ray projection image. A pattern recognition algorithm as known in the art may be used to identify the tip of the extraction device, or another salient feature of the extraction device, in the projection images.

The processing unit 3 may also be adapted for registering the live stream of x-ray projection image data, e.g. each two-dimensional image frame of the stream, to the three-dimensional data. For example, the three-dimensional parametric model representative of the spatial configuration of the lead as present in the body of the subject before performing said extraction procedure may be registered to the live stream of x-ray projection image data, e.g. to each frame, and/or the segmented three-dimensional image obtained by an image segmentation of the lead may be registered to the live stream of x-ray projection image data, e.g. to each frame, and/or the three-dimensional image data, corresponding to a medical three-dimensional imaging modality, of at least a part of the body of the subject that contains the lead, acquired before the extraction procedure, may be registered to the live stream of x-ray projection image data, e.g. to each frame.

Registration techniques as known in the art may be applied. For example, a 3D-2D registration algorithm may be used, e.g. a 3D model to 2D image or a 2D projection image to 3D volumetric image registration. The registration may comprise a first step of determining a rigid transformation, e.g. which maps the coordinates of the 2D image frame onto the coordinate system of the 3D model or volumetric image. The registration may comprise a second step of determining an elastic transformation, e.g. to compensate for a deformation due to the patient position on the table during the extraction procedure (which may differ from the position in which the 3D data was acquired), due to breathing and/or due to cardiac motion. Furthermore, the processing unit 3 may also be adapted for determining a suitable viewing angle for the acquiring the live stream of x-ray projection image data based on the 3D data, e.g. for suggesting to a user an optimal projection angle.

Furthermore, the processing unit 3 may also be adapted for registering the live stream of x-ray projection image data to the three-dimensional data by taking positioning information of the extraction device into account. For example, the extraction device may be adapted for providing positioning information, e.g. by fiber optical shape sensing and/or electromagnetic tracking, as known in the art.

The device 1 also comprises an output 4. The output 4 may comprise a connector for connecting to a display device, or the output may comprise a display device. For example, the output 4 may be a computer monitor or video display unit. It is an advantage of embodiments of the present invention that 3D image data, such as a CT volumetric image can be visualized during an extraction intervention.

In an embodiment, the output 4 is adapted for generating and outputting an image of a cross-sectional view of the lead and/or of its surrounding body structure, e.g. a blood vessel or heart chamber, at the determined position of the extraction device based on the three-dimensional image data.

The output 4 may provide image data, e.g. display images and/or a video sequence of images and/or display a continuously or frequently update image. For example, the output 4 may provide an image based on the 3D image data, e.g. a CT volumetric image, in which the determined position of the extraction device is indicated.

The image of the cross-sectional view may be a dynamic CT cross section at the location, e.g. as determined, of the distal end of the extraction device. The output 4 may also provide a plurality of images, e.g. a plurality of cross sectional views of the body structure, for example showing a plurality of locations spaced forward from or around the determined location of the extraction device in the longitudinal direction of a blood vessel. For example, slices showing the next 5 or 10 mm ahead of the extraction device may be provided.

Figure 7:
FIG. 7 shows an exemplary cross-sectional image as generated in accordance with embodiments of the present invention.

An exemplary image of such cross-sectional view is shown in FIG. 7.

Furthermore, the output 4 may also be adapted for generating and outputting an image of a longitudinal view of the lead and/or of its surrounding body structure at the determined position of the extraction device based on the three-dimensional image data.

Figure 8:
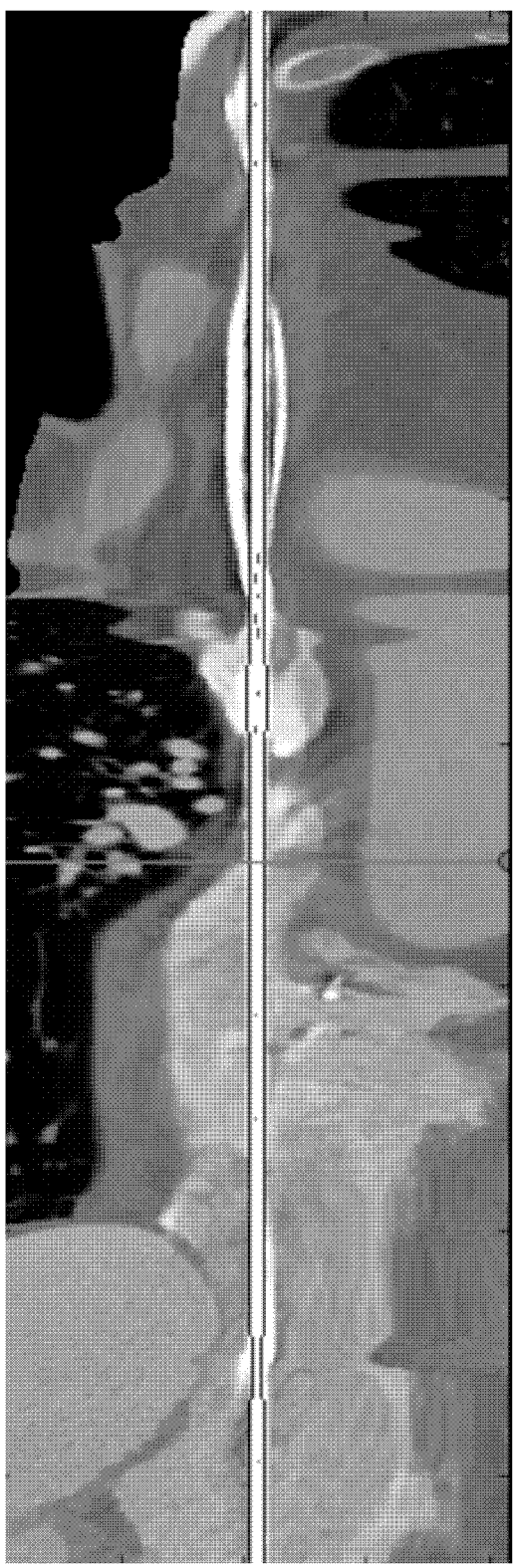
FIG. 8 and FIG. 9 show exemplary images of longitudinal views as generated in accordance with embodiments of the present invention.
Figure 9:
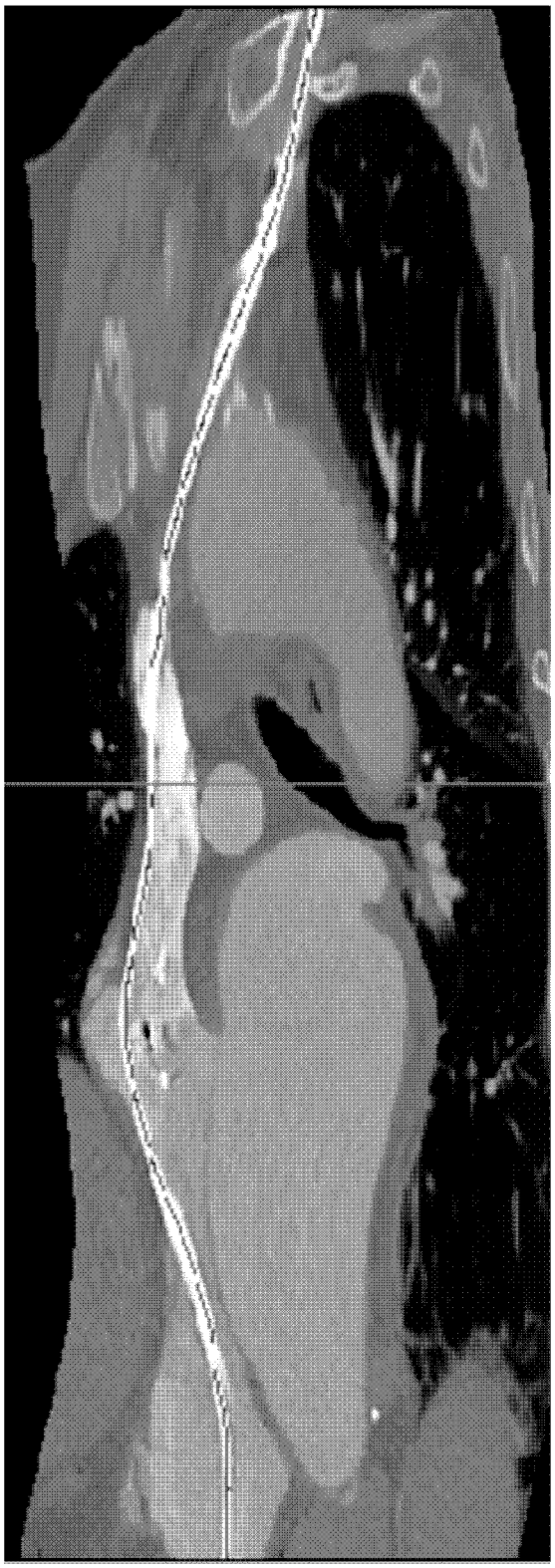

Exemplary images of such longitudinal views are shown in FIG. 8 and FIG. 9.

Furthermore, the 3D image data may comprise a plurality of 3D images, e.g. a sequence images taken during a cardiac cycle and/or a sequence showing the flow of a contrast agent through the body structure, e.g. a blood vessel. Therefore, the output 4 may also be adapted for generating and outputting an image or images, substantially as discussed hereinabove, for each of such a plurality of 3D images.

The output may generate the image or images by a multiplanar reformation or multiple plane reconstruction (MPR) or maximum intensity projection (MIP) at the current position of extraction device, e.g. of the tip of the extraction device or a tip position adapted MIP.

Thus, while navigating the extraction device, it can be advantageously tracked in the live x-ray image in relation to the registered lead tip and CT image information may be displayed of a local neighbourhood of the extraction device, e.g. in the vicinity of the lead, for guidance.

The output may also generate and output an overlay image of information extracted from the three-dimensional image data onto the projection image data, such as a segmentation of the lead and/or of the surrounding body structure, e.g.; blood vessel, projected onto the projection image data (taking a registration of the projection image data and the three-dimensional image data into account).

The output may compose a plurality of different generated images, e.g. as described hereinabove, into a user interface.

Figure 10:
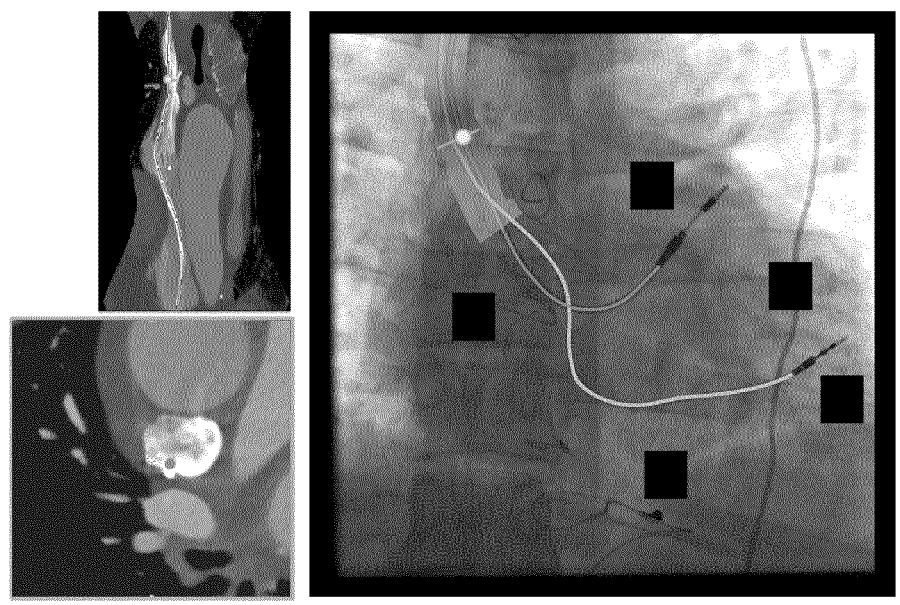
FIG. 10 illustrates an exemplary combination of images as may be generated in accordance with embodiments of the present invention.

An exemplary overlay image in a composed user interface view is shown in FIG. 10.

It is an advantage that a user of the device during the extraction procedure can easily determine from the provided image or images how close to the vessel wall the lead body is at the location of the extraction device.

It is an advantage that a user of the device during the extraction procedure can easily determine from the provided image or images if the extraction device is near the lead, e.g. near an embedded tip of the lead.

It is an advantage that a user of the device during the extraction procedure can easily determine from the provided image or images if lead-to-lead binding could be present, e.g. based on how a contrast agent flows between leads and the location of the leads relative to each other.

Even though the 3D image data, e.g. CT information, is static, e.g. pre-acquired before the extraction procedure, and body structures may deform during the procedure as traction is placed on the lead and/or adjacent leads are taken out, projecting the cross-sectional view at the position of the extraction device and/or views from 5 to 10 mm in front of the extraction device can still offer valuable information to the operator. For example, binding and adhesion of the lead at the present position can be visualized or even quantified. This can be confirmed during the procedure, e.g. by exerting traction on the lead and looking for the lead moving independently of the vessel to indicate no or low adhesion.

The output 4 may also provide additional information. For example, the output 4 may be adapted for outputting the local curvature and/or the degree of local adhesion at the determined position of the extraction device. For example, advice may be provided for changing the extraction device. For example, information may be provided, e.g. displayed, that relates to curvature ahead of the extraction device and/or to proximity of the lead to the vessel wall.

In a preferred embodiment, the output 4 comprises an interface for controlling at least one parameter of the extraction device 7, such as parameters of a laser or mechanical extraction device. For example, vessel and/or plaque characteristics at (or near) the determined position of the extraction device may be determined from the 3D image data, and the parameter of the extraction device 7 may be controlled by taking these characteristics into account. For example, the power and/or wavelength of a laser extraction device, or the power of mechanical cutting device, may be controlled to be lower for soft plaque regions than for hard plaque regions. Furthermore, extraction device may be turned on and off based on its detected position to avoid accidentally harming the vessel wall. For example, after a region with hard plaque where a strong pressure needs to be applied to advance the extraction device, an unexpected sudden advance of the cutting tip, once the hard plaque is passed, could cause damage to the vessel. This can be advantageously avoided by automatically turning off the cutting device in regions with low adhesion, or after the characteristic sudden advance after a region with hard plaque.

Controlling the at least one parameter of the extraction device 7 may also comprise controlling separate active elements of the extraction device, e.g. turning the elements individually on and off or modulating the power of the elements individually. Thus, an asymmetric ablation of the tissue can be achieved. For example, depending on the vessel geometry, the tissue surrounding the lead may only require to be cut from one side of the lead. Also the plaque composition on different sides of the lead may differ. The curvature of the vessel or the lead location relative to the vessel wall may require an asymmetric ablation by the laser catheter to avoid harm to sensitive sections of the vessel. By using the image information, such asymmetric cutting behaviour may be automatically regulated.

For example, controlling the at least one parameter may comprise controlling an angular power distribution of the extraction device, e.g. of a laser extraction device and/or of a mechanical extraction device.

Controlling the at least one parameter may take the image data into account, but may also (e.g. additionally) take sensor data into account, e.g. from a sensor on the extraction device, such as a force sensor, an optical sensor, an ultrasound sensor or other such sensor devices as known in the art.

Furthermore, the device may be adapted for generating an indication (e.g. providing a message via the output) for informing a physician performing the extraction procedure, while moving along the lead, that it could be advisable to switch from a laser extraction device to a mechanical extraction device.

In a second aspect, the present invention relates to an integrated system for providing information and/or for controlling equipment in an interventional radiology room or heart catherization laboratory, in which the system comprises a device in accordance with embodiments of the first aspect of the present invention.

A system in accordance with embodiments of the second aspect of the present invention may also comprise the extraction device 7.

In a third aspect, the present invention relates to a method for providing image data during an extraction procedure for extracting a lead from the body of a subject using an extraction device.

Figure 2:
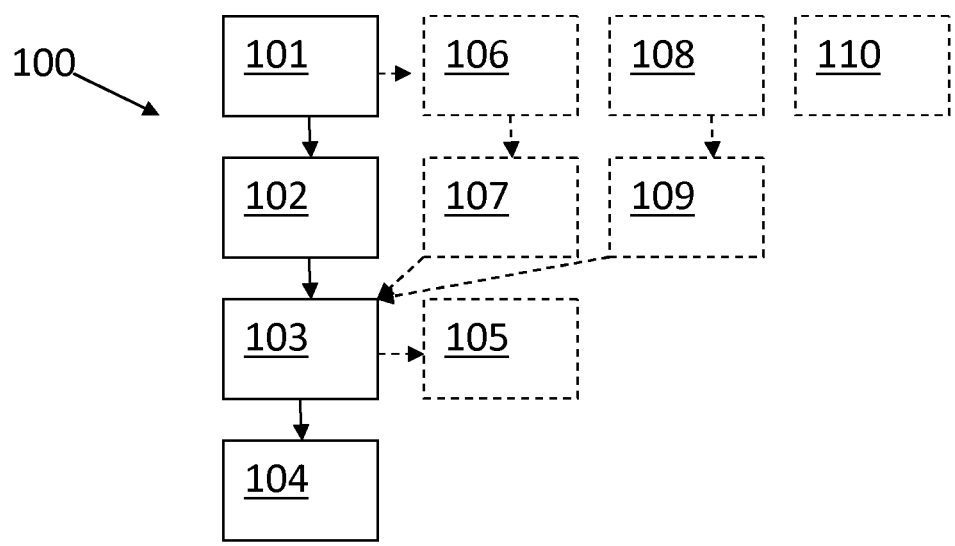
FIG. 2 schematically illustrates a method in accordance with embodiments of the present invention.

Referring to FIG. 2, an exemplary method 100 in accordance with embodiments of the present invention is shown.

The method 100 comprises receiving 101 three-dimensional image data representative of, e.g. showing, the lead in the body of the subject as acquired before performing said extraction procedure. For example, the method may comprise acquiring the 3D image data before the extraction procedure, e.g. using a medical imaging scanner, such as a CT or MRI scanner. For example, the method may comprise receiving a contrast-enhanced cardiac computed tomography dataset of the thorax and the heart of the subject.

The method comprises receiving 102 a live stream of x-ray projection image data of the lead in the body of the subject during the extraction procedure. For example, the live stream may comprise images acquired by an x-ray fluoroscopy imaging device.

The method comprises determining 103 a position of the extraction device in the three-dimensional image data by detecting a position of the extraction device in the live stream of x-ray projection image data during the extraction procedure and correlating this position in the live stream with the position in the three-dimensional image data.

The method further comprises controlling 105 at least one parameter of the extraction device. For example, the method may comprise determining a vessel and/or plaque characteristic at or near the determined position of the extraction device. Controlling 105 the at least one parameter may take this characteristic into account.

In an embodiment, the method may further comprise generating and outputting 104 an image of a crossectional view of the lead and/or its surrounding body structure, e.g. a blood vessel or heart chamber, at the determined position based on the three-dimensional image data.

For example, the method may comprise generating and outputting a plurality of images of cross sectional views of the lead and/or its surrounding body structure at a plurality of locations spaced forward from or spaced around the determined position of the extraction device in the three-dimensional image data in the longitudinal direction of the lead and/or of the longitudinal direction of the body structure, e.g. of a blood vessel. For example, the images may correspond to positions in the longitudinal direction in a range of 2 cm, e.g. 1 cm, e.g. 0.5 cm, on either side of the position of the extraction device, or in a range extending 2 cm, e.g. 1 cm, e.g. 0.5 cm, forward from the extraction device.

The method may comprise generating and outputting a further image of a longitudinal view of the lead and/or its surrounding body structure at the determined position of the extraction device based on the three-dimensional image data.

The at least one parameter of the extraction device may comprise a power setting and/or an on/off setting of the extraction device.

This controlling 105 may comprise (e.g. temporarily) deactivating the extraction device when the detected position corresponds to a region of low adhesion of the lead to the vessel wall and/or a softer region after a hard plaque.

The method may comprise segmenting 106 the lead from the three-dimensional image data to provide a segmented three-dimensional image.

The method may comprise registering 107 the segmented three-dimensional image to the live stream of x-ray projection image data to correlate the detected position of the extraction device in the live stream of x-ray projection image data with the position in the three-dimensional image data.

The method may comprise fitting 108 a three-dimensional parametric model of the lead, e.g. a deformable wire model, to the segmented three-dimensional image such that the fitted three-dimensional parametric model is representative of the spatial configuration of the lead as present in the body of the subject before performing said extraction procedure.

The method may comprise registering 109 the fitted three-dimensional parametric model to the live stream of x-ray projection image data to correlate the detected position of the extraction device in the live stream of x-ray projection image data with the position in the three-dimensional image data.

The method may also comprise determining 110 a parameter as function of a longitudinal position along the lead based on the three-dimensional image data and/or the fitted three-dimensional parametric model. The method may comprise outputting this parameter corresponding to a longitudinal position at or ahead (e.g. at a predetermined distance ahead of, e.g. 2 cm, e.g. 1 cm, e.g. 0.5 cm) of the determined position of the extraction device.

The parameter may comprise a local curvature and/or a degree of local adhesion of the lead and/or a proximity of the lead to the vessel wall.

The method may comprise determining the degree of local adhesion to the vessel wall by quantifying a local motion of the lead relative to the vessel wall from a temporal sequence of three-dimensional image data and determining a degree of local adhesion based on the local motion.

In a further aspect, the present invention relates to a computer program product for performing a method in accordance with embodiments of the third aspect of the present invention when executed by a computing device. For example, steps of such method may be implemented by handcrafted (e.g. human-coded) deterministic algorithms and/or in parts or in total by machine learning or deep learning methods trained to solve the algorithmic task.

Figure 3:
FIG. 3 shows a photograph of an exemplary lead extraction device, for illustrating aspects of embodiments of the present invention.

Referring to FIG. 3, a photograph of an exemplary lead extraction device 7 is shown, e.g. which can be used in combination with embodiments of the present invention.

Figure 4:
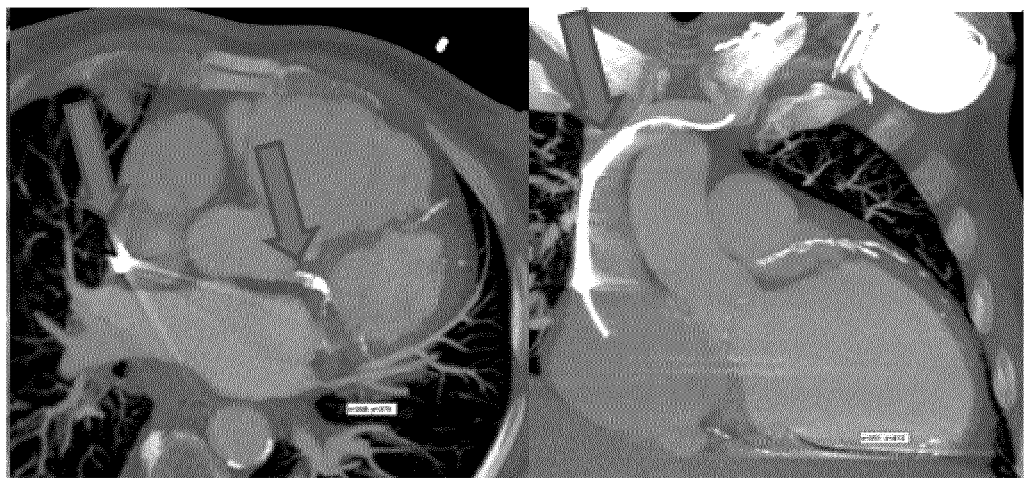
FIG. 4 shows slices of a cardiac computed tomography volumetric image with leads in the imaging plane, for illustrating aspects of embodiments of the present invention.

FIG. 4 shows slices of a cardiac CT 3D image with leads in the imaging plane, as indicated by arrows. No metal artefact correction was applied in this example.

Figure 5:
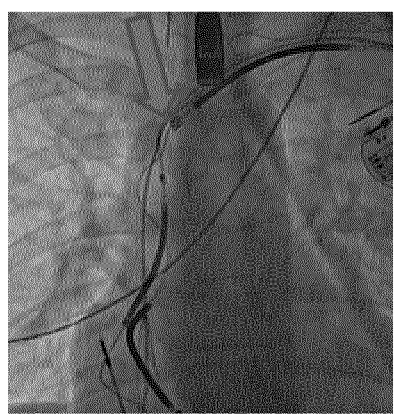
FIG. 5 shows an x-ray projection in which the lead extraction device is advancing along the lead, for illustrating embodiments of the present invention.

FIG. 5 shows an x-ray projection in which the lead extraction device is advancing along the lead. The tip position is indicated by an arrow.

Figure 6:
FIG. 6 shows extracted leads after an extraction procedure, for illustrating embodiments of the present invention.

FIG. 6 shows extracted leads after an extraction procedure.

As used herein, the term "or" should be interpreted as a disjunctive "or." Further, the term "or" and the term "and" when prefaced by the term "at least one of" or the term by "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B, both A and B, or combinations of one or more of A and B, and such other combinations as relevant to the recited list or terms consistent with the corresponding description in the specification.

The invention claimed is:

1. A device for providing image data during an extraction procedure for extracting a lead in a body of a subject using an extraction device, the device comprising:
    an input interface configured to receive a live stream of x-ray projection image data of the lead in the body of the subject during the extraction procedure and to receive three-dimensional image data representative of the lead in the body of the subject as acquired before performing the extraction procedure,
    a processor configured to determine a position of the extraction device in the three-dimensional image data by detecting a position of the extraction device in the live stream of x-ray projection image data during the extraction procedure and correlating the position in the live stream with the position in the three-dimensional image data, and
    an output interface configured to control at least one parameter of the extraction device,
    wherein the processor is further configured to i) determine a vessel or plaque characteristic at or near the determined position of the extraction device and ii) control the at least one parameter of the extraction device by taking the characteristic into account.

2. The device of claim 1, wherein the output interface is further configured to generate and output an image of a cross-sectional view of the lead or of a body structure surrounding the lead at the determined position of the extraction device based on the three-dimensional image data.

3. The device of claim 2, wherein the output interface is configured to generate and output a plurality of images of cross-sectional views of the lead or the body structure at a plurality of locations spaced forward from or spaced around the determined position of the extraction device in the three-dimensional image data in a longitudinal direction of the lead or of a longitudinal direction of the body structure.

4. The device of claim 2, wherein the output interface is configured to generate and output a further image of a longitudinal view of the lead or the body structure at the determined position of the extraction device based on the three-dimensional image data.

5. The device of claim 1, wherein the at least one parameter of the extraction device comprises a power setting, an on/off setting, an angular power distribution of the extraction device.

6. The device of claim 5, wherein the processor is configured to deactivate the extraction device when the detected position of the extraction device corresponds to a region with low adhesion or a softer region after a hard plaque.

7. The device of claim 1, further comprising a preprocessor configured to pre-process the three-dimensional image data by segmenting the lead from the three-dimensional image data to provide a segmented three-dimensional image.

8. The device of claim 7, wherein the processor is configured to register the segmented three-dimensional image to the live stream of x-ray projection image data to correlate the detected position of the extraction device in the live stream of x-ray projection image data with the position in the three-dimensional image data.

9. The device of claim 7, wherein the pre-processor is configured to fit a three-dimensional parametric model of the lead to the segmented three-dimensional image such that the fitted three-dimensional parametric model is representative of the spatial configuration of the lead as present in the body of the subject before performing the extraction procedure, and wherein the processor is configured to register the fitted three-dimensional parametric model to the live stream of x-ray projection image data to correlate the detected position of the extraction device in the live stream of x-ray projection image data with the position in the three-dimensional image data.

10. The device of claim 9, wherein the pre-processor is configured to determine a parameter as a function of a longitudinal position along the lead based on the three-dimensional image data or the fitted three-dimensional parametric model, and wherein the output interface is configured to output the parameter corresponding to a longitudinal position at or ahead of the determined position of the extraction device, wherein the parameter comprises a local curvature, a degree of local adhesion of the lead, or a proximity of the lead to a vessel wall.

11. The device of claim 10, wherein the pre-processor is configured to determine the degree of local adhesion to the vessel wall by quantifying a local motion of the lead relative to the vessel wall from a temporal sequence of three-dimensional image data received via the input interface and to determine a degree of local adhesion based on the local motion.

12. The device of claim 1, wherein the three-dimensional image data comprises a contrast-enhanced cardiac computed tomography dataset of a thorax and a heart of the subject.

13. An integrated system for providing information or for controlling equipment in an operating room, interventional radiology room or heart catherization laboratory, the system comprising a device in accordance with claim 1.

14. A method for providing image data during an extraction procedure for extracting a lead in a body of a subject using an extraction device, the method comprising:
receiving three-dimensional image data representative of the lead in the body of the subject as acquired before performing the extraction procedure;
receiving a live stream of x-ray projection image data of the lead in the body of the subject during the extraction procedure;
determining a position of the extraction device in the three-dimensional image data by detecting a position of the extraction device in the live stream of x-ray projection image data during the extraction procedure and correlating the position in the live stream with the position in the three-dimensional image data;
determining a vessel or plaque characteristic at or near the determined position of the extraction device and controlling at least one parameter of the extraction device taking the characteristic into account and,
generating and outputting an image of a cross-sectional view of the lead and/or a body structure surrounding the lead at the determined position of the extraction device based on the three-dimensional image data.

15. The method of claim 14, further comprising generating and outputting an image of a cross-sectional view of the lead or of a body structure surrounding the lead at the determined position of the extraction device based on the three-dimensional image data.

16. The method of claim 14, further comprising generating and outputting a plurality of images of cross-sectional views of the lead or the body structure at a plurality of locations spaced forward from or spaced around the determined position of the extraction device in the three-dimensional image data in a longitudinal direction of the lead or of a longitudinal direction of the body structure.

17. The method of claim 14, further comprising generating and outputting a further image of a longitudinal view of the lead or the body structure at the determined position of the extraction device based on the three-dimensional image data.

18. The method of claim 14, wherein the at least one parameter of the extraction device comprises a power setting, an on/off setting, or an angular power distribution of the extraction device.

19. The method of claim 14, further comprising pre-processing the three-dimensional image data by segmenting the lead from the three-dimensional image data to provide a segmented three-dimensional image and registering the segmented three-dimensional image to the live stream of x-ray projection image data to correlate the detected position of the extraction device in the live stream of x-ray projection image data with the position in the three-dimensional image data.

20. A non-transitory computer readable medium having stored thereon instructions that when executed by processing circuitry of a system for providing image data during an extraction procedure for extracting a lead in the body of a subject using an extraction device causes the processing circuitry to:
receive three-dimensional image data representative of the lead in the body of the subject as acquired before performing the extraction procedure;
receive a live stream of x-ray projection image data of the lead in the body of the subject during the extraction procedure;
determine a position of the extraction device in the three-dimensional image data by detecting a position of the extraction device in the live stream of x-ray projection image data during the extraction procedure and correlating the position in the live stream with the position in the three-dimensional image data;
determine a vessel or plaque characteristic at or near the determined position of the extraction device and controlling at least one parameter of the extraction device taking the characteristic into account; and
generate and output an image of a cross-sectional view of the lead or a body structure surrounding the lead at the determined position of the extraction device based on the three-dimensional image data.

* * * * *